United States Patent
Li et al.

(10) Patent No.: US 7,361,691 B2
(45) Date of Patent: Apr. 22, 2008

(54) METHOD OF TREATING CANCERS USING β-LAPACHONE OR ANALOGS OR DERIVATIVES THEREOF

(75) Inventors: Chiang Li, West Roxbury, MA (US); Youzhi Li, Dedham, MA (US)

(73) Assignee: Arqule, Inc., Woburn, MA (US)

( * ) Notice: Subject to any disclaimer, the term of this patent is extended or adjusted under 35 U.S.C. 154(b) by 589 days.

(21) Appl. No.: 10/726,467

(22) Filed: Dec. 2, 2003

(65) Prior Publication Data

US 2005/0119352 A1    Jun. 2, 2005

Related U.S. Application Data

(60) Provisional application No. 60/430,288, filed on Dec. 2, 2002.

(51) Int. Cl.
*A61K 31/506* (2006.01)
*A61K 31/497* (2006.01)

(52) U.S. Cl. .................. 514/682; 514/252.18
(58) Field of Classification Search ........... 514/682, 514/252.18
See application file for complete search history.

(56) References Cited

U.S. PATENT DOCUMENTS

| | | | | |
|---|---|---|---|---|
| 5,424,073 | A | 6/1995 | Rahman et al. | 424/450 |
| 5,763,625 | A | 6/1998 | Boothman et al. | 549/390 |
| 5,824,700 | A | 10/1998 | Frydman et al. | 514/454 |
| 5,969,163 | A | 10/1999 | Frydman et al. | 549/389 |
| 6,245,807 | B1 | 6/2001 | Pardee et al. | 514/454 |
| 6,458,974 | B1 | 10/2002 | Jiang et al. | 549/389 |
| 6,664,288 | B1 * | 12/2003 | Pardee et al. | 514/449 |
| 6,998,391 | B2 * | 2/2006 | Lyons et al. | 514/49 |
| 7,070,797 | B2 * | 7/2006 | Pardee et al. | 424/422 |
| 2003/0091639 | A1 | 5/2003 | Jiang et al. | 424/486 |

FOREIGN PATENT DOCUMENTS

| | | |
|---|---|---|
| WO | WO 94/04145 | 3/1994 |
| WO | WO 00/61142 | 10/2000 |
| WO | WO 03/086497 A1 * | 10/2003 |
| WO | WO 03/090710 A1 | 11/2003 |
| WO | WO 2004/007531 A2 | 1/2004 |
| WO | WO 2004/045557 A2 | 6/2004 |

OTHER PUBLICATIONS

George et al. American Family Physician. 1999, vol. 59/No. 7, electronic copy, pp. 1-12.*
Goodman & Gilman's The Pharmacological Basis of Therapeutics (1996): pp. 1225-1232.*
Topay et al. Synergistic activity of the new ABL-specific tyrosine kinase inhibitor ST1571 and chemotherapeutic drugs on BCR-ABL-positive chronic myelogenous leukemia cells. Leukemia (2001), 15:342-347, electronic copy pp. 1-13.*
DiChenna, et al., *J. Med. Chem.*, 44:2486-2489 (2001).
Goncalves, et al., *Mol. Biochem. Parasitol.*, 1:167-176 (1980).
Gupta, et al., *Curr. Sci.*, 46(10):337 (1977).
Gupta, et al., *Indian J. Chem.*, 16B:35-37 (1978).
Li, et al., *Mol. Med.*, 6(12):1008-1015 (2000).
Li, et al., *Proc. Natl. Acad. Sci. USA*, 96(23):13369-13374 (1999).
Li, et al., *Proc. Natl. Acad. Sci. USA*, 100(5):2674-2678 (2003).
Li, et al., *Mol. Med.*, 5:232-239 (1999).
Maruyama, et al., *Chem. Lett.*, 847-850 (1977).
McGlynn, et al., *Eur. J. Biochem.*, 207:265-275 (1992).
Portela, et al., *Biochem. Pharmacol.*, 51:275-282(1996).
Schaffner-Sabba, et al., *J. Med. Chem.*, 27:990-994 (1984).
Sun, et al., *Tetrahedron Lett.*, 39:8221-8224 (1998).

* cited by examiner

*Primary Examiner*—Brian-Yong S. Kwon
*Assistant Examiner*—Charleswort Rae
(74) *Attorney, Agent, or Firm*—Mintz, Levin, Cohn, Ferris, Glovsky and Popeo, P.C.; Ivor R. Elrifi; Matthew Pavao (57) ABSTRACT

Cancers and/or malignancies can be treated by administration of a cell cycle checkpoint activator, which is preferably β-lapachone, or a derivative or analog thereof, combined with an oncogenic kinase modulator, preferably imatinib. This combination of the cell cycle checkpoint activator with the oncogenic kinase modulator results in an unexpectedly greater than additive (i.e., synergistic) apoptosis in cancer cells. The invention includes methods of treating cancers by administering the combination of the cell cycle checkpoint activator and the oncogenic kinase modulator, pharmaceutical compositions comprising the combination of drugs used in these methods, as well as pharmaceutical kits.

19 Claims, 4 Drawing Sheets

METHOD OF TREATING CANCERS USING β-LAPACHONE OR ANALOGS OR DERIVATIVES THEREOF

RELATED APPLICATIONS

This application claims priority to U.S. Ser. No. 60/430,288, filed on Dec. 2, 2002 which is incorporated by reference in its entirety.

BACKGROUND OF THE INVENTION

Cancer kills hundreds of thousands of people every year in the United States alone, and many more cases of cancer are diagnosed each year. Despite advances in the treatment of certain forms of cancer (including surgery, radiotherapy, and chemotherapy), many types of cancer are essentially incurable. Even when an effective treatment is available for a certain cancer, the side effects of such treatment are often severe and can result in a significant decrease in quality of life.

While there are many forms of cancer, all cancers are characterized by inappropriate cell proliferation. Multiple checkpoints are built into the machinery of the cell proliferation cycle where cells make a commitment to repair DNA damage or to undergo cell death. Unlike normal cells, cancer cells have lost checkpoint control and have an uncontrolled proliferation drive. The approximately $10^{16}$ cell multiplications in the human lifetime, together with inevitable errors in DNA replication and exposure to ultraviolet rays and mutagens, underscores the requirement for checkpoint functions. Major checkpoints occur at G1/S phase and at the G2/M phase transitions where cells make a commitment to repair DNA or undergo apoptosis. Cells are generally thought to undergo apoptosis when DNA damage is irreparable (Li, C J et al. (1999) *Proc. Natl. Acad. Sci. USA* 96:13369-13374).

Identification of therapeutic agents modulating the checkpoint control may improve cancer treatment. Indeed, recent reports suggest that activation of cell cycle checkpoints may represent an important new paradigm in the treatment of cancer (see, e.g., Y. Li et al., *Proc. Natl. Acad. Sci. USA* (2003), 100(5), 2674-8). The cell cycle checkpoint activator β-lapachone, which acts at the G1/S phase transition, has been found to exhibit significant anti-tumor activity against a range of tumor types both in vitro and in animal studies while exhibiting a favorable side effect profile, leading to the initiation of human clinical trials. In addition, it has been reported that β-lapachone induces necrosis in human breast cancer cells, and apoptosis in ovary, colon, and pancreatic cancer cells through induction of caspase (Li, Y Z et al., (1999) *Molecular Medicine* 5:232-239).

It has also been reported that β-lapachone, when combined with Taxol® (paclitaxel; Bristol-Myers Squibb Co., N.Y., N.Y.) at moderate doses, has effective anti-tumor activity in human ovarian, prostate and breast cancer xenograft models in nude mice. No signs of toxicity to the mice were observed, and no weight loss was recorded during the subsequent two months following treatment during which the tumors did not reappear (See Li, C J et al. (1999) *Proc. Natl. Acad. Sci. USA* 96:13369-13374). Taxol is believed to act at the G2/M phase transition of the cell cycle.

Many conventional chemotherapy agents cause damage to cancerous and non-cancerous cells alike. While this broad-spectrum activity allows the chemotherapy to kill many different types of cancers, it often also results in damage to normal cells. The therapeutic index of such compounds (a measure of the ability of the therapy to discriminate between normal and cancerous cells) can be quite low; frequently, a dose of a chemotherapy drug that is effective to kill cancer cells will also kill normal cells, especially those normal cells (such as epithelial cells) which undergo frequent cell division. When normal cells are affected by the therapy, side effects such as hair loss, suppression of hematopoesis, and nausea can occur.

Recent advances in cancer chemotherapeutics have resulted in the development of new "targeted" anti-cancer agents, designed to affect biological targets that are primarily associated with cancerous cells, rather than normal cells. Examples of such agents include imatinib (sold by Novartis under the trade name Gleevec in the United States), gefitinib (developed by Astra Zeneca under the trade name Iressa), and erlotinib (being developed under the name of Tarceva by Genentech, OSI, and Roche). While such agents can be quite effective against the intended cellular target, and can have lower rates of side effects than conventional chemotherapies, targeted therapies are, by design, effective only against cells expressing the biological target. Cancer cells which do not express this specific target, or which express a mutated form of the target, may be less affected by a targeted agent. These agents are therefore of limited utility.

Despite the progress made to date in discovering new anti-tumor treatments, new treatments for cancer are needed.

Receptor tyrosine kinases are large enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR) which possesses tyrosine kinase activity is mutated and/or overexpressed in many human cancers such as brain, lung, squamous cell, bladder, gastric, breast, head and neck, oesophageal, gynecological and thyroid tumors.

Accordingly, it has been recognized that inhibitors of receptor tyrosine kinases are useful as a selective inhibitors of the growth of mammalian cancer cells. For example, erbstatin, a tyrosine kinase inhibitor selectively attenuates the growth in athymic nude mice of a transplanted human mammary carcinoma which expresses epidermal growth factor receptor tyrosine kinase but is without effect on the growth of another carcinoma which does not express the EGF receptor.

SUMMARY OF THE INVENTION

It has now been discovered that the combination of a cell cycle checkpoint activator, such as β-lapachone (or a derivative or analog thereof) with a oncogenic kinase modulator (such as imatinib) provides unexpectedly effective treatment for certain cancers.

In one embodiment, the present invention relates to a method for treating cancer in a subject by administering to the subject a cell cycle checkpoint activator, which is preferably β-lapachone, or a derivative or analog thereof, together with a oncogenic kinase modulator, such as imatinib, in a therapeutically effective amount, under conditions such that the cancer is treated. In one embodiment, the oncogenic kinase modulator is an tyrosine kinase modulator. In another embodiment, the tyrosine kinase modulator is an epidermal growth factor receptor signal transduction pathway modulator or a Bcr-Abl signal transduction pathway modulator. In another embodiment, the a Bcr-Abl signal transduction pathway modulator is imatinib. In other embodiments the cancer is cancer is selected from the group consisting of multiple myeloma, chronic myelogenous leukemia, pancreatic cancer, non-small cell lung cancer, lung cancer, breast cancer, colon cancer, ovarian cancer, prostate cancer, malignant melanoma, non-melanoma skin cancers, hematologic tumors, hematologic tumors, hematologic malignancies, childhood leukemia, childhood lymphomas, multiple myeloma, Hodgkin's disease, lymphomas of lymphocytic origin, lymphomas of cutaneous origin, acute leukemia, chronic leukemia, acute lymphoblastic leukemia, acute myelocytic leukemia, chronic myelocytic leukemia, plasma cell neoplasm, lymphoid neoplasm and cancers associated with AIDS. In another embodiment, the subject is a human.

The cell cycle checkpoint activator, and the oncogenic kinase modulator are administered intravenously, intraperitoneally, or orally. They are administered simultaneously or in any order. In preferred embodiments, their times of administration are up to 24 hours apart. Optionally, they are contained within separate vials to be administered sequentially or simultaneously.

The oncogenic kinase modulator is administered at a dosage from about 10 mg/day to about 2000 mg/day. In one embodiment, the oncogenic kinase modulator is administered at a dosage of about 250 or 500 mg/day. In another embodiment, the oncogenic kinase modulator, imatinib, is administered at 400, 600, or 800 mg/day. In some embodiments, the cell cycle checkpoint activator is administered at a dosage, from about 100 to 500,000 µg per kilogram body weight of recipient per day, from about 1000 to 250,000 µg per kilogram body weight of recipient per day, or from about 10,000 to 150,000 µg per kilogram body weight of recipient per day. In other embodiments, the cell cycle checkpoint activator is administered at a dosage from about 2 mg/m$^2$ to 5000 mg/m$^2$ per day, from about 20 mg/m$^2$ to 500 mg/m$^2$ per day, or from about 30 to 300 mg/m$^2$ per day.

In a preferred embodiment, the cell cycle point activator further comprises a pharmaceutically acceptable carrier. This carrier is Poloxamer, Povidone K17, Povidone K12, Tween 80, ethanol, Cremophor/ethanol, polyethylene glycol (PEG) 400, propylene glycol, Trappsol, alpha-cyclodextrin or analogs thereof, beta-cyclodextrin or analogs thereof, or gamma-cyclodextrin or analogs thereof.

The invention also includes a kit for the treatment of a malignancy in a subject comprising separate vials containing β-lapachone or a derivative, or analog thereof and an oncogenic kinase modulator, with instructions for administering β-lapachone first. Preferably, the oncogenic kinase modulator in the kit is imatinib. Preferably, the cancer treated by the kit is pancreatic cancer, non-small cell lung cancer, multiple myeloma, or chronic myelogenous leukemia.

In a preferred embodiment, the invention includes a method of treating cancer in a subject by administering to the subject a therapeutically effective amount of β-lapachone or a derivative or analog thereof, and an oncogenic kinase modulator, such that the cancer is treated.

In another preferred embodiment, the invention includes a method of treating cancer in a subject by administering to the subject a therapeutically effective amount of β-lapachone or a derivative or analog thereof, and imatinib, such that the cancer is treated.

In another preferred embodiment, the invention includes a method of treating multiple myeloma or chronic myelogenous leukemia in a human by administering to the subject a therapeutically effective amount of β-lapachone or a derivative or analog thereof, and imatinib, such that the multiple myeloma or chronic myelogenous leukemia is treated.

In another preferred embodiment, the invention includes a method of treating pancreatic cancer or non-small cell lung cancer in a human by administering to the subject a therapeutically effective amount of β-lapachone or a derivative or analog thereof, and imatinib, such that the pancreatic cancer or non-small cell lung cancer is treated.

In another aspect, the invention provides kits useful for the treatment of cancer. The kits comprise at least one container, the at least one container containing a cell cycle checkpoint activator (preferably β-lapachone or a derivative or analog thereof), and an oncogenic kinase modulator (preferably imatinib), together with instructions for administering the cell cycle checkpoint activator and the oncogenic kinase modulator to a subject to treat cancer. Preferably, the kit contains instructions describing the use of a cell cycle checkpoint activator and an oncogenic kinase modulator to treat cancer, e.g. pancreatic cancer or non-small cell lung cancer.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

DETAILED DESCRIPTION OF THE INVENTION

This invention provides methods for treating individuals afflicted with cancer, such as multiple myeloma and other tumors and/or malignancies. The methods include the step of administering to an individual afflicted with cancer an effective amount of a cell cycle checkpoint activator, such as β-lapachone or a derivative or analog thereof, together with an effective amount of an oncogenic kinase modulator such as imatinib, such that the cancer is treated.

The term "oncogenic kinase modulator" refers to compositions which inhibit or enhance the kinase activity of members of mitogenic signal pathways in cells which are involved in carcinogenesis. The kinases involved include tyrosine and serine/threonine kinases. Preferably, the oncogenic kinase modulator inhibits or enhances the kinase activity of tyrosine kinases (is a tyrosine kinase modulator). In two preferable embodiments, the oncogenic kinase modulator inhibits or enhances the kinase activity of a member of the epidermal growth factor receptor signal transduction pathway (is an EGFR signal transduction pathway modulator) or the Bcr-Abl signal transduction pathway (is a Bcr-Abl signal transduction pathway modulator).

The term "EGFR signal transduction pathway modulator" refers to compositions that can effect the signaling capacity of members of the EGFR signal transduction pathway. The epidermal growth factor (EGF) family of receptor tyrosine kinases consists of four receptors, EGFR (ErbB1), ErbB2 (Neu), ErbB3, and ErbB4. Members of the EGFR family contain a cytoplasmic tyrosine kinase domain, a single transmembrane domain, and an extracellular domain that is involved in ligand binding and receptor dimerization. Activation of the EGFR results in the initiation of a diverse array of cellular pathways. In response to toxic environmental stimuli, such as ultraviolet irradiation, or to receptor occupation by EGF, the EGFR forms homo- or heterodimers with other family members. Each dimeric receptor complex will initiate a distinct signaling pathway by recruiting different Src homology 2 (SH2)-containing effector proteins. Dimerization results in autophosphorylation initiating a downstream cascade of events culminating in cellular responses such as cell proliferation or apoptosis. The activated EGFR dimer complexes with the adapter protein, Grb, coupled to the guanine nucleotide releasing factor, SOS. The Grb-SOS complex can either bind directly to phosphotyrosine sites in the receptor or indirectly through Shc. These protein interactions bring SOS in close proximity to Ras, allowing for Ras activation. This subsequently activates the ERK and JNK signaling pathways that, in turn, activate transcription factors, such as c-fos, AP-1, and Elk-1, that promote gene expression and contribute to cell proliferation. The EGFR signal transduction pathway modulator can modulate the activity of any member of the EGF signal transduction pathway, inhibiting or enhancing their function.

In one embodiment, the EGFR signal transduction pathway modulator acts upon the EGFR itself. In a preferred embodiment, the EGFR signal transduction pathway modulator inhibits the activity of the EGFR. In a more preferred embodiment, the EGFR signal transduction pathway modulator inhibits the tyrosine kinase activity of the EGFR. Gefitinib and erlotinib can act on the EGFR by inhibiting tyrosine kinase activity. This receptor-specific enzyme activity is a key factor in the signal transmission in a host of mammalian cells, including human cells, especially epithelial cells, cells of the immune system and cells of the central and peripheral nervous system. The EGF-induced activation of the receptor-associated protein tyrosine kinase (EGFR-PTK) is, in many cells, a prerequisite for cell division and hence for the proliferation of a cell population. The addition of EGFR-specific tyrosine kinase inhibitors thus inhibits the replication of these cells.

The inhibition of the EGFR-specific protein tyrosine kinase (EGFR-PTK) can be demonstrated, inter alia, by the method of E. McGlynn et at., Europ. J. Biochem. 207, 265-275 (1992).

The term "Bcr-Abl signal transduction pathway modulator" refers to compositions that can effect the signaling capacity of members of the Bcr-Abl signal transduction pathway. A common theme of the tyrosine phosphorylation of Bcr-Abl substrates is the consequent activation of multiple signal transduction cascades shared by haemopoietic cytokines known to influence growth and differentiation of haemopoietic cells. First, Ras activation in Bcr-Abl-expressing cells is mediated by Bcr-Abl's interaction with the adaptor signalling molecules Grb2, Shc, Sos and Dok. The sum of these interactions results in the favouring of Ras in its active GTP-bound form. This in turn leads to the activation of Raf-1's serine/threonine kinase activity with the subsequent activation of the MAP kinase kinase (MEK) pathway (resulting in promitotic transcriptional regulation) and the PI3K (phosphoinositide 3-kinase) pathway (by phosphorylation of Akt, which leads, via Bad phosphorylation and dissociation from Bcl-$X_L$, to an anti-apoptotic signal mediated by BCl-$X_L$). Bcr-Abl-dependent activation of the PI3K pathway has also been shown to be mediated by Bcr-Abl interaction with the adaptor molecule Crkl. The guanine-nucleotide-exchange factor Vav is known to interact with and act as a phosphorylation substrate of Bcr-Abl. This activated Vav subsequently favours the existence of Rac in its active GTP-bound state, leading to its effects on cytoskeletal reorganisation. The activation of STAT1 and 5 by phosphorylation has been shown in Bcr-Abl-expressing cells, although the mediators of this activation remain unclear. STAT1 and 5 phosphorylation results in their translocation to the nucleus, where they activate transcription. Bcr-Abl inhibits the proteosomal degradation of Fusion Protein (Fus) by a protein kinase C βII (PKCβII) mechanism. Fus regulates nucleocytoplasmic export and RNA processing, thereby altering myeloid transcription factor CCAAT/enhancer-binding protein α (C/EBPα) expression, with subsequent effects on myeloid transcriptional regulation.

The terms "subject" or "patient" are art-recognized, and as used herein, refer to a mammal, including dog, cat, rat, mouse, monkey, cow, horse, goat, sheep, pig, camel, and, most preferably, a human. In preferred embodiments, a subject is a subject in need of treatment. In certain embodiments, the subject can be a normal subject, e.g., a subject having no known or diagnosed abnormal cells, e.g., a cancer-free subject. In other embodiments, the subject has a known, diagnosed, or suspected disorder, i.e., a cell proliferative disorder such as a benign or malignant tumor, including cancer, e.g., a solid or liquid tumor.

The term "treating" is art-recognized, and as used herein refers to preventing, reducing, ameliorating, or curing a condition (such as cancer) for which such treatment is indicated. the progress of such treatment can be monitored, e.g., by measures known in the art, some of which are described herein.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer,) and the health of the patient should preferably be closely monitored during and for a reasonable period after treatment.

The term "cell cycle checkpoint activator," as used herein, refers to a compound capable of activating cell cycle checkpoints, e.g., by activating checkpoint-mediated DNA repair mechanisms, or by reinstating checkpoint activity that has been lost due to a malfunction or mutation in the cellular pathways that regulate cell cycle activity. As is known in the art, major cell cycle checkpoints occur at $G_1$/S phase and at the $G_2$/M phase transitions. Modulation of cell cycle checkpoint activation is further discussed in, e.g., C. J. Li et al. Proc. Natl. Acad. Sci. USA (1999), 96(23), 13369-13374, and Y. Li et al. Proc. Natl. Acad. Sci. USA (2003), 100(5), 2674-2678, and PCT Publication WO 00/61142 (Pardee et al.). Preferred cell cycle checkpoint activators for use in the present invention induce checkpoint activation (i.e., activate one or more cell cycle checkpoints, preferably at $G_1$/S phase), preferably without causing substantial DNA damage. In addition, certain preferred cell cycle checkpoint activators are capable of increasing the level or activity of E2F (more preferably E2F1) in a cell. Methods for screening for cell cycle checkpoint activators, including compounds capable of elevating E2F activity or levels in a cell, include those that are disclosed in PCT Patent Application No. PCT/US03/22631 to Li et al., the contents of which is incorporated herein by reference. In certain embodiments, preferred cell cycle checkpoint activators are capable of increasing the level or activity of E2F in a cell by an amount sufficient to cause apoptosis if the cell is a cancerous cell. More preferred cell cycle checkpoint activators are capable of raising the level or activity of E2F1 in a cell by an amount sufficient to cause apoptosis if the cell is a cancerous cell.

The term "effective amount" is art-recognized, and as used herein, refers to an amount effective to achieve a desired result, such as preventing, treating, ameliorating, or curing. When the term "effective amount" is used in reference to one or more components of a combination therapy, the amount is an amount effective when employed in combination with such other component or components.

As further used herein, the phrase "β-lapachone" refers to 3,4-dihydro-2,2-dimethyl-2H-naphtho[1,2-b]pyran-5,6-dione, and has the chemical structure:

β-lapchone, or analogs and derivatives thereof, in accordance with the present invention, can be synthesized as described in U.S. Pat. No. 6,458,974, which is incorporated by reference herein in its entirety. Preferred derivatives and analogs are discussed below.

The methods of the present invention comprise the step of administering to the patient, in combination, an effective amount of a cell cycle checkpoint activator (such as β-lapachone), in combination with an oncogenic kinase modulator. Preferably, the combination is (1) a cell cycle checkpoint activator such as β-lapachone or its derivatives or analogs; and (2) oncogenic kinase modulators such as imatinib, gefitinib, and erlotinib; and pharmaceutically acceptable salts thereof. A non-limiting list of representative compounds useful in this invention is provided in Tables 1 and 2, infra.

In one embodiment, the invention is directed to a method for treating a subject having malignant cells, or inhibiting further growth of such malignant cells, by administering a drug or compound that activates checkpoints in the cell cycle. A second drug or compound that modulates a member of the EGFR signal transduction pathway is administered simultaneously with or following or preceding the checkpoint-activating drug or compound. Individual compounds satisfying these criteria are known to those of ordinary skill in the art. For example, β-lapachone is an activator of the G1/S phase checkpoint, while imatinib and other oncogenic kinase modulators are oncogenic kinase modulators. A list of representative checkpoint activators is set forth below in Table 1:

TABLE 1

| Type | Category | Compound Name | Chemical Formula |
|---|---|---|---|
| 1. | G1/S phase drug | β-lapachone<br>Reduced β-lapachone | 3,4-dihydro-2,2-dimethyl-2H-naphtho[1,2-b]pyran-5,6-dione |
| 2. | G1 phase drug | Lovastatin | [1s[1α(R*), 3α7β,8β S*,4s*),8αβ]]-Methylbutanoic acid 1,2,3,7,8,8a-hexahydro-3,7-dimethyl-8-[2-(tetrahydor-4-hydroxy-6-0x0-2H-pyran-2-yl)ethyl[-1-naphthalenyl ester |
| 3. | G1 phase drug | Mimosine | α-Amino-3-hydroxy-4oxo-1(4H)-pyridine propanoic acid |
| 4. | G1 phase drug | Tamoxifen | [Z]-2-[4-(1,2-Diphenyl-1-butenyl)-phenoxy]-N,N-dimethylethanamine |

A list of representative oncogenic kinase modulators useful in the present invention is provided in Table 2.

TABLE 2

| Type | Category | Compound Name | Proprietary Name | Structure |
|---|---|---|---|---|
| 1. | Bcr-Abl Tyrosine kinase inhibitor | Imatinib | Gleevec | |

TABLE 2-continued

| Type | Category | Compound Name | Proprietary Name | Structure |
|---|---|---|---|---|
| 2. | EGFR Tyrosine kinase inhibitor | Gefitinib | Iressa |  |
| 3. | EGFR Tyrosine kinase inhibitor | Erlotinib | Tarceva |  |
| 4. | EGFR Tyrosine kinase inhibitor | Tyrphostin 51 | N/A |  |
| 5 | EGFR Tyrosine kinase inhibitor | Lavendustin A | N/A |  |
| 6. | EGFR Tyrosine kinase inhibitor | Tyrphostin 25 | N/A |  |
| 7. | EGFR Tyrosine kinase inhibitor | Tyrphostin 47 | N/A |  |
| 8. | EGFR Tyrosine kinase inhibitor | Erbstatin analog | N/A |  |

TABLE 2-continued

| Type | Category | Compound Name | Proprietary Name | Structure |
|---|---|---|---|---|
| 9. | EGFR Tyrosine kinase inhibitor | Tyrphostin 25 | N/A | |
| 10. | EGFR Tyrosine kinase inhibitor | AG-494 | N/A | |
| 11. | EGFR Tyrosine kinase inhibitor | HDBA (Lavendustin C) | N/A | |
| 12. | EGFR Tyrosine kinase inhibitor | RG-13022 | N/A | |
| 13. | EGFR Tyrosine kinase inhibitor | RG-14620 | N/A | |
| 14. | EGFR Tyrosine kinase inhibitor | Lavendustin B | N/A | |
| 15. | EGFR Tyrosine kinase inhibitor | Tyrphostin 46 | N/A | |

TABLE 2-continued

| Type | Category | Compound Name | Proprietary Name | Structure |
|---|---|---|---|---|
| 16. | EGFR Tyrosine kinase inhibitor | AG-825 | N/A | |
| 17. | EGFR Tyrosine kinase inhibitor | Tyrphostin AG-1478 | N/A | |

The combinations of the present invention (i.e. β-lapachone and imatinib) are particularly advantageous as synergistic results are obtained. (See Examples infra). Synergistci results are obtained when.

When a checkpoint activator is administered in combination with an oncogenic kinase modulator, the active agents may be administered simultaneously, or, alternatively, may be administered separately. When administered simultaneously, the agents can be administered as part of a single formulation (e.g., both active agents formed as part of a single pill, or co-dissolved in a common solvent), or as part of two separate dosage forms (e.g., two separate pills, one pill and one intravenous solution, and the like). The particular form and timing of administration will be selected by one of ordinary skill in the art, considering factors such as those described elsewhere herein (e.g., the health of the patient, the possibility of drug-drug interactions, and the like). If the two agents are not administered simultaneously, they should be administered within a time interval suitable to achieve the objectives of the invention, e.g., within one week, one day, or one hour. For example, if the cell cycle checkpoint activator is administered first, administration of the oncogenic kinase modulators should preferably occur within one week, more preferably within about two days, and still more preferably within about one day after the cell cycle checkpoint activator is administered. Preferably, the cell cycle checkpoint activator is administered prior to, or simultaneously with, an oncogenic kinase modulators.

As described above, preferred checkpoint activating compounds include G1/S phase drugs (for example, β-lapachone), and G1 phase drugs (for example, lovastatin, mimosine, tamoxifen, and the like). β-lapachone, its derivatives and analogs are most preferred.

Formula Ia

Preferred derivatives of beta-lapachone include reduced β-lapachone (Formula Ia, in which R' and R" are each hydrogen), as well as derivatives of reduced beta-lapachone (Formula Ia, in which R' and R" are each independently hydrogen, lower alkyl, or acyl).

Preferred combinations include:

β-lapachone with imatinib; β-lapachone with gefitinib; β-lapachone with erlotinib;

Reduced β-lapachone with imatinib; reduced β-lapachone with gefitinib; reduced β-lapachone with erlotinib.

Lovastatin with imatinib; lovastatin with gefitinib; lovastatin with erlotinib;

Mimosine with imatinib; mimosine with gefitinib; mimosine with erlotinib;

Tamoxifen with imatinib; tamoxifen with gefitinib; tamoxifen with erlotinib.

The combination of the present invention results in a surprising synergy which is beneficial in reducing tumor burden load and/or regressing tumor growth, especially in patients with metastatic disease.

Preferably, the human malignancy treated is a cancer such as pancreatic cancer, non-small cell lung cancer, multiple myeloma, or leukemia, although the invention is not limited in this respect, and other metastatic diseases may be treated by the combination of the present invention. For example, the human malignancy treated could also be a cancer forming solid tumors, such as lung, breast, colon, ovarian, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In another embodiment, the checkpoint activating compounds and oncogenic kinase modulators of the invention are used to inhibit the growth of cancer cells, or kill cancer cells outright. The cancer cells can be inhibited or killed in vitro, in vivo, or ex vivo. In preferred embodiments the cancer cells are from solid tumors, such as lung, breast, colon, ovarian, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS. In other preferred embodiments the cancer cells are cell lines. Cell lines that are inhibited or killed by the checkpoint activating compounds and oncogenic kinase modulators of the invention include ARH-77 multiple myeloma cells and K562 human chorionic myelogenous leukemia cells. In other preferred embodiments, the checkpoint activating compound is β-lapachone, lovastatin, mimosine, or tamoxifen. In other preferred embodiments, the oncogenic kinase modulator is imatinib, gefitinib, or erlotinib.

The individual components of the combination of the present invention will be addressed in more detail below.

The oncogenic kinase modulator, such as imatinib, may be administered in any manner found appropriate by a clinician in generally accepted efficacious dose ranges, such as those described in the prescribing materials for imatinib provided by the manufacturer.

In general, the oncogenic kinase modulator, is administered orally at dosages from about 1 mg/day to about 1000 mg/day, preferably from about 250 mg/day to about 500 mg/day, and most preferably about, 150 mg/day, 250 mg/day or 500 mg/day. Preferably, imatinib is administered orally at 400, 600, or 800 mg/day. Preferably, gefitinib is administered orally at 250 or 500 mg/day. Preferably, erlotinib is administered orally at 100 mg/day. It is preferred that dosages be administered over a time period of about 1 to about 24 hours, and typically over a period of about 3 hours. Dosage for can occur once per week, with dosages repeated from 1 to about 4 weeks or more, preferably from about 2 to about 3 weeks.

As previously mentioned, the oncogenic kinase modulator, will be administered in a similar regimen with a checkpoint activator, such as β-lapachone or a derivative or analog thereof, although the amounts will preferably be reduced from that normally administered. It is preferred, for example, that the oncogenic kinase modulator be administered at the same time or after checkpoint activator (e.g., β-lapachone) has been administered to the patient. When the oncogenic kinase modulator is administered after β-lapachone, the oncogenic kinase modulator is advantageously administered about 24 hours after the β-lapachone has been administered.

Preferably, a compound such as β-lapachone (or a derivative or analog thereof) is administered to a patient in at least one dose in the range of 100 to 500,000 μg per kilogram body weight of recipient per day, more preferably in the range of 1000 to 250,000 μg per kilogram body weight per day, most preferably in the range of 10000 to 150,000 μg per kilogram body weight per day. Doses can also be expressed in units of mg/m²; as an example, a suitable dose of beta-lapachone for a human subject is preferably in the range of 2 mg/m to 5000 mg/m², more preferably 20 mg/m² to 500 mg/m² (still more preferably 30 to 300 mg/m²) when dosage is by intravenous infusion once weekly. The desired dose is suitably administered once or in several more sub-doses administered at appropriate intervals (e.g., once per week, once per day, divided doses administered throughout the day, or other appropriate schedule). These sub-doses may be administered as unit dosage forms, for example, containing 1 to 20,000 μg, preferably 10 to 10,000 μg per unit dosage form. Repeated doses can be administered as appropriate. Due to the water insolubility of β-lapachone, pharmaceutical carriers or solubilizing agents may be used to provide sufficient quantities of β-lapachone for use in the treatment methods of the present invention (see, e.g., U.S. Patent Publication 20030091639 to Jiang et al., the contents of which is incorporated herein by reference).

As mentioned above, preferred modulators of cell cycle checkpoint activation for use in the present invention induce checkpoint activation, preferably without causing substantial DNA damage. In addition, preferred modulators of cell cycle checkpoint activation are capable of increasing the level or activity of E2F (more preferably E2F1) in a cell. Methods for screening for modulators of cell cycle checkpoint activation, including compounds capable of elevating E2F activity or levels in a cell, include methods such as those disclosed in PCT Patent Application No. PCT/US03/22631 to Li et al., the contents of which are incorporated herein by reference. Certain assays for determining cell death or survival are also disclosed in PCT Patent Application No. PCT/US03/22631; such assays are useful for determining compounds effective for killing cancerous cells, e.g., as described in Examples 1 and 2, below.

The combination of the present invention is particularly advantageous in the treatment of patients who have chemotherapeutically refractive metastatic cancers.

While β-lapachone is the preferred checkpoint activating compound for use in the composition in accordance with the present invention, the invention is not limited in this respect, and β-lapachone derivatives or analogs, such as lapachol, and pharmaceutical compositions and formulations thereof are part of the present invention. Such β-lapachone analogs include, without limitation, those recited in PCT International Application PCT/US93/07878 (WO 94/04145), which is incorporated by reference herein in its entirety, and which discloses compounds of the formula:

where R and $R_1$ are each independently hydrogen, substituted and unsubstituted aryl, substituted and unsubstituted alkenyl, substituted and unsubstituted alkyl and substituted or unsubstituted alkoxy. The alkyl groups preferably have from 1 to about 15 carbon atoms, more preferably from 1 to about 10 carbon atoms, still more preferably from 1 to about

6 carbon atoms. The term alkyl unless otherwise modified refers to both cyclic and noncyclic groups, although of course cyclic groups will comprise at least three carbon ring members. Straight or branched chain noncyclic alkyl groups are generally more preferred than cyclic groups. Straight chain alkyl groups are generally more preferred than branched. The alkenyl groups preferably have from 2 to about 15 carbon atoms, more preferably from 2 to about 10 carbon atoms, still more preferably from 2 to 6 carbon atoms. Especially preferred alkenyl groups have 3 carbon atoms (i.e., 1-propenyl or 2-propenyl), with the allyl moiety being particularly preferred. Phenyl and napthyl are generally preferred aryl groups. Alkoxy groups include those alkoxy groups having one or more oxygen linkage and preferably have from 1 to 15 carbon atoms, more preferably from 1 to about 6 carbon atoms. The substituted R and $R_1$ groups may be substituted at one or more available positions by one or more suitable groups such as, for example, alkyl groups such as alkyl groups having from 1 to 10 carbon atoms or from 1 to 6 carbon atoms, alkenyl groups such as alkenyl groups having from 2 to 10 carbon atoms or 2 to 6 carbon atoms, aryl groups having from six to ten carbon atoms, halogen such as fluoro, chloro and bromo, and N, O and S, including heteroalkyl, e.g., heteroalkyl having one or more hetero atom linkages (and thus including alkoxy, aminoalkyl and thioalkyl) and from 1 to 10 carbon atoms or from 1 to 6 carbon atoms.

Other β-lapachone analogs contemplated in accordance with the present invention include those described in U.S. Pat. No. 6,245,807, which is incorporated by reference herein in its entirety, and which discloses β-lapachone analogs and derivatives having the structure:

where R and $R_1$ are each independently selected from hydrogen, hydroxy, sulfhydryl, halogen, substituted alkyl, unsubstituted alkyl, substituted alkenyl, unsubstituted alkenyl, substituted aryl, unsubstituted aryl, substituted alkoxy, unsubstituted alkoxy, and salts thereof, where the dotted double bond between the ring carbons represents an optional ring double bond.

Additional β-lapachone analogs and derivatives are recited in PCT International Application PCT/US00/10169 (WO00/61142), which is incorporated by reference herein in its entirety, and which discloses compounds of the structure:

where $R_5$ and $R_6$ may be independently selected from hydroxy, $C_1$-$C_6$ alkyl, $C_1$-$C_6$ alkenyl, $C_1$-$C_6$ alkoxy, $C_1$-$C_6$ alkoxycarbonyl, —$(CH_2)_n$-phenyl; and $R_7$ is hydrogen, hydroxyl, $C_1$-$C_6$ alkyl, $C_1$-$C_6$ alkenyl, $C_1$-$C_6$ alkoxy, $C_1$-$C_6$ alkoxycarbonyl, —$(CH_2)_n$-amino, —$(CH_2)_n$-aryl, —$(CH_2)_n$-heteroaryl, —$(CH_2)_n$-heterocycle, or —$(CH_2)_n$-phenyl, wherein n is an integer from 0 to 10.

Other β-lapachone analogs and derivatives are disclosed in U.S. Pat. Nos. 5,763,625, 5,824,700, 5,969,163, as well is in scientific journal articles, such as Sabba et al., *J Med Chem* 27:990-994 (1984), which discloses β-lapachone with substitutions at one or more of the following positions: 2-, 8- and/or 9-positions. See also Portela et al., *Biochem Pharm* 51:275-283 (1996) (substituents at the 2- and 9-positions); Maruyama et al., *Chem Lett* 847-850 (1977); Sun et al., *Tetrahedron Lett* 39:8221-8224 (1998); Goncalves et al., *Molecular and Biochemical Parasitology* 1:167-176 (1998) (substituents at the 2- and 3-positions); Gupta et al., *Indian Journal of Chemistry* 16B: 35-37 (1978); Gupta et al., *Curr Sci* 46:337 (1977) (substituents at the 3- and 4-positions); DiChenna et al., *J Med Chem* 44: 2486-2489 (2001) (monoarylamino derivatives). Each of the above-mentioned references are incorporated by reference herein in their entirety.

More preferably, β-lapachone analogs and derivatives contemplated by the present application are intended to encompass compounds having the general formula I and II:

Formula I

Formula II where the dotted double bond between the ring carbons represents an optional ring double bond and where R and $R_1$ are each independently selected from hydrogen, hydroxy, sulfhydryl, halogen, substituted alkyl, unsubstituted alkyl, substituted alkenyl, unsubstituted alkenyl, substituted aryl, unsubstituted aryl, substituted alkoxy, unsubstituted alkoxy, and salts thereof. The alkyl groups preferably have from 1 to about 15 carbon atoms, more preferably from 1 to about 10 carbon atoms, still more preferably from 1 to about 6 carbon atoms. The term alkyl refers to both cyclic and noncyclic groups. Straight or branched chain noncyclic alkyl groups are generally more preferred than cyclic groups. Straight chain alkyl groups are generally more preferred than branched. The alkenyl groups preferably have from 2 to about 15 carbon atoms, more preferably from 2 to about 10 carbon atoms, still more preferably from 2 to 6 carbon atoms. Especially preferred alkenyl groups have 3 carbon atoms (i.e., 1-propenyl or 2-propenyl), with the allyl moiety being particularly preferred. Phenyl and napthyl are generally preferred aryl groups. Alkoxy groups include those alkoxy groups having one or more oxygen linkage and preferably have from 1 to 15 carbon atoms, more preferably from 1 to about 6 carbon atoms. The substituted R and $R_1$ groups may be substituted at one or more available positions by one or more suitable groups such as, for example, alkyl groups having from 1 to 10 carbon atoms or from 1 to 6 carbon atoms, alkenyl groups having from 2 to 10 carbon atoms or 2 to 6 carbon atoms, aryl groups having from six to ten carbon atoms, halogen such as fluoro, chloro and bromo, and N, O and S, including heteroalkyl, e.g., heteroalkyl having one or more hetero atom linkages (and thus including alkoxy, aminoalkyl and thioalkyl) and from 1 to 10 carbon atoms or from 1 to 6 carbon atoms; and where $R_5$ and $R_6$ may be independently selected from hydroxy, $C_1$-$C_6$ alkyl, $C_1$-$C_6$ alkenyl, $C_1$-$C_6$ alkoxy, $C_1$-$C_6$ alkoxycarbonyl, —$(CH_2)_n$-aryl, —$(CH_2)_n$-heteroaryl, —$(CH_2)_n$-heterocycle, or —$(CH_2)_n$-phenyl; and $R_7$ is hydrogen, hydroxyl, $C_1$-$C_6$ alkyl, $C_1$-$C_6$ alkenyl, $C_1$-$C_6$ alkoxy, $C_1$-$C_6$ alkoxycarbonyl, —$(CH_2)_n$-amino, —$(CH_2)_n$-aryl, —$(CH_2)_n$-heteroaryl, —$(CH_2)_n$-heterocycle, or —$(CH_2)_n$-phenyl, wherein n is an integer from 0 to 10.

Preferred β-lapachone analogs and derivatives also contemplated by the invention include compounds of the following general formula III:

Formula III where $R_1$ is $(CH_2)_n$—$R_2$, where n is an integer from 0-10 and $R_2$ is hydrogen, an alkyl, an aryl, a heteroaromatic, a heterocyclic, an aliphatic, an alkoxy, an allyloxy, a hydroxyl, an amine, a thiol, an amide, or a halogen.

Analogs and derivatives also contemplated by the invention include 4-acetoxy-β-lapachone, 4-acetoxy-3-bromo-β-lapachone, 4-keto-β-lapachone, 7-hydroxy-β-lapachone, 7-methoxy-β-lapachone, 8-hydroxy-β-lapachone, 8-methoxy-β-lapachone, 8-chloro-β-lapachone, 9-chloro-β-lapachone, 8-methyl-β-lapachone and 8,9-dimethoxy-β-lapachone.

Other β-lapachone analogs and derivatives also contemplated by the invention include compounds of the following general formula IV:

Formula IV where $R_1$-$R_4$ are each, independently, selected from the group consisting of H, $C_1$-$C_6$ alkyl, $C_1$-$C_6$ alkenyl, $C_1$-$C_6$ alkoxy, $C_1$-$C_6$ alkoxycarbonyl, —$(CH_2)_n$-aryl, —$(CH_2)_n$-heteroaryl, —$(CH_2)_n$-heterocycle, or —$(CH_2)_n$-phenyl; or $R_1$ and $R_2$ combined are a single substituent selected from the above group, and $R_3$ and $R_4$ combined are a single substituent selected from the above groups, in which case —— is a double bond.

Preferred β-lapachone analogs and derivatives also contemplated by this invention include dunnione and 2-ethyl-6-hydroxynaphtho[2,3-b]-furan-4,5-dione.

Preferred β-lapachone analogs and derivatives also contemplated by the invention include compounds of the following general formula V:

Formula V where $R_1$ is selected from H, $CH_3$, $OCH_3$ and $NO_2$.

Additional preferred β-lapachone analogs useful in the methods and kits of the invention are represented by Formula VI (see also the co-owned PCT patent application entitled "Novel Lapachone Compounds and Methods of Use Thereof", filed Nov. 18, 2003, and claiming priority to U.S. provisional application No. 60/427,283, filed Nov. 18, 2002, both of which are incorporated herein by reference):

VI or pharmaceutically acceptable salts thereof, or a regioisomeric mixture thereof, wherein R1-R6 are each, independently, selected from the group consisting of H, OH, substituted and unsubstituted $C_1$-$C_6$ alkyl, substituted and unsubstituted $C_1$-$C_6$ alkenyl, substituted and unsubstituted $C_1$-$C_6$ alkoxy, substituted and unsubstituted $C_1$-$C_6$ alkoxycarbonyl, substituted and unsubstituted $C_1$-$C_6$ acyl, —$(CH_2)_n$-amino, —$(CH_2)_n$-aryl, —$(CH_2)$-heterocycle, and —$(CH_2)_n$-phenyl; or one of R1 or R2 and one of R3 or R4; or one of R3 or R4 and one of R5 or R6 form a fused ring, wherein the ring has 4-8 ring members; R7-R10 are each, independently, hydrogen, hydroxyl, halogen, substituted or unsubstituted alkyl, substituted or unsubstituted alkoxy, nitro, cyano or amide; and n is an integer from 0 to 10.

In a preferred embodiment, R1 and R2 are alkyl, R3-R6 are, independently, H, OH, halogen, alkyl, alkoxy, substituted or unsubstituted acyl, substituted alkenyl or substituted alkyl carbonyl, and R7-R10 are hydrogen. In another preferred embodiment, R1 and R2 are each methyl and R3-R10 are each hydrogen. In another preferred embodiment, R1-R4 are each hydrogen, R5 and R6 are each methyl and R7-R10 are each hydrogen.

Additional preferred β-lapachone analogs useful in the methods and kits of the invention are represented by Formula VII (see also the co-owned PCT patent application entitled "Novel Lapachone Compounds and Methods of Use Thereof", filed Nov. 18, 2003, incorporated herein by reference):

VII or pharmaceutically acceptable salts thereof, or a regioisomeric mixture thereof, wherein R1-R4 are each, independently, selected from the group consisting of H, OH, substituted and unsubstituted $C_1$-$C_6$ alkyl, substituted and unsubstituted $C_1$-$C_6$ alkenyl, substituted and unsubstituted $C_1$-$C_6$ alkoxy, substituted and unsubstituted $C_1$-$C_6$ alkoxycarbonyl, substituted and unsubstituted $C_1$-$C_6$ acyl, —(CH$_2$)$_n$-amino, —(CH$_2$)$_n$-aryl, —(CH$_2$)$_n$-heterocycle, and —(CH$_2$)$_n$-phenyl; or one of R1 or R2 and one of R3 or R4 form a fused ring, wherein the ring has 4-8 ring members; R5-R8 are each, independently, hydrogen, hydroxyl, halogen, substituted or unsubstituted alkyl, substituted or unsubstituted alkoxy, nitro, cyano or amide; and n is an integer from 0 to 10. In certain embodiments of Formula VII, R1, R2, R3, R4, R5, R6, R7 and R8 are not each simultaneously H.

In light of the teachings herein, one of ordinary skill in the art will be able to screen potential cell cycle checkpoint activators and oncogenic kinase modulators to determine which combinations of the two are useful in the methods and kits of the present invention, using no more than routine experimentation. Further, in vivo methods for testing the efficacy of the combination of a checkpoint activator and an oncogenic modulator are disclosed in C. J. Li et al. *Proc. Natl. Acad. Sci. USA* (1999), 96(23), 13369-13374.

As with the use of other chemotherapeutic drugs, the individual patient will be monitored in a manner deemed appropriate by the treating physician. Dosages can be reduced, e.g., if severe neutropenia or severe peripheral neuropathy occurs, or if a grade 2 or higher level of mucositis is observed, using the Common Toxicity Criteria of the National Cancer Institute.

The combination therapy agents described herein may be administered singly and sequentially, or in a cocktail or combination containing both agents or one of the agents with other therapeutic agents, including but not limited to, immunosuppressive agents, potentiators and side-effect relieving agents. For example, a dose of the cell cycle checkpoint activator drug component (e.g., β-lapachone) is administered at least one hour (more preferably at least 2 hours, 4 hours, 8 hours, 12 hours, or 24 hours) prior to administration of a dose of the oncogenic kinase modulator, e.g., imatinib. The therapeutic agents will preferably be administered orally, intravenously or otherwise systemically by injection intramuscularly, subcutaneously, intrathecally or intraperitoneally.

Pharmaceutical compositions useful in the methods and kits of this invention may exist in the dosage form as a solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, nontoxic carriers or diluents, which are vehicles commonly used to formulate pharmaceutical compositions for animal or human administration. The diluent is preferably selected so as not to adversely affect the biological activity of the active agent or agents. Examples of such diluents are distilled water, physiological saline, Ringer's solution, dextrose solution, and Hank's solution. A preferred carrier for the solubilization of β-lapachone is hydroxypropyl beta cyclodextrin, a water-solubilizing carrier molecule (see, e.g., U.S. Patent Publication 20030091639, incorporated by reference herein). Other water-solubilizing agents for combining with β-lapachone or other modulators of cell cycle checkpoint activation, such as Poloxamer, Povidone K17, Povidone K12, Tween 80, ethanol, Cremophor/ethanol, polyethylene glycol 400, propylene glycol and Trappsol, are contemplated. Furthermore, the invention is not limited to water-solubilizing agents, and oil-based solubilizing agents such as lipiodol and peanut oil, may also be used.

Polymeric carriers can also be used to administer an active agent according to this invention, e.g., a cell cycle checkpoint activator such as beta-lapachone (see, e.g., PCT Publication No. WO03090710, which is incorporated herein by reference). Biocompatible polymers carrying an active agent may be provided in the form of microspheres, nanospheres, millirods, or other shapes or forms known to one of ordinary skill in the art.

In addition, the pharmaceutical composition or formulation may also include other carriers, adjuvants, or nontoxic, nontherapeutic, nonimmunogenic stabilizers and the like. Effective amounts of such diluent or carrier will be those amounts which are effective to obtain a pharmaceutically acceptable formulation in terms of solubility of components, or biological activity, and the like. Liposome formulations, are also contemplated by the present invention, and have been described See, e.g. U.S. Pat. No. 5,424,073, which is herein incorporated by reference.

For the purposes of the present invention, the cell cycle checkpoint activator drugs or compounds, and the oncogenic kinase modulators or compounds, or derivatives or analogs thereof, described herein include their pharmacologically acceptable salts, preferably sodium, potassium, lithium, mesylate, lactate and the like; ammonium or substituted ammonium salts, preferably secondary or tertiary ammonium salts. Further, the active compounds described herein may be conjugated to a water-soluble polymer or may be derivatized with water-soluble chelating agents or radionuclides. Examples of water soluble polymers are, but not limited to: polyglutamic acid polymer, copolymers with polycaprolactone, polyglycolic acid, polyactic acid, polyacrylic acid, poly(2-hydroxyethyl 1-glutamine), carboxymethyl dextran, hyaluronic acid, human serum albumin, polyalginic acid or a combination thereof. Examples of water-soluble chelating agents are, but not limited to: DIPA (diethylenetriaminepentaacetic acid), EDTA, DTTP, DOTA or their water-soluble salts, etc. Examples of radionuclides include, but not limited to: $^{111}$In, $^{90}$Y, $^{166}$Ho, $^{68}$Ga, $^{99m}$Tc, and the like.

Although intravenous administration is sometimes preferred as discussed above, the invention is not intended to be limited in this respect, and the compounds can be administered by any means known in the art. Such modes include oral, rectal, nasal, topical (including buccal and sublingual) or parenteral (including subcutaneous, intramuscular, intravenous and intradermal) administration.

For ease of administration and comfort to the patient, oral administration is often preferred. However, oral administration typically requires the administration a higher dose than intravenous administration. The skilled artisan can determine which form of administration is best in a particular case, balancing dose needed versus the number of times (e.g., per day, per week, or per month) administration is necessary.

In administering a checkpoint activator compound such as β-lapachone, the normal dose of such compound individually is utilized as set forth above. However, when combination therapies are used, it is preferable to use a lower dosage—typically 75% or less of the individual amount, more preferably 50% or less, still more preferably 40% or less. The term "effective amount," as used herein, refers to an amount effective to treat the disease condition in combination with any other active agent in a combination regimen according to the invention.

In therapeutic applications, the dosages of the agents used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and more preferably causing complete regression of the cancer. A therapeutically effective amount of a pharmaceutical agent is that which provides an objectively identifiable improvement as noted or measured by the patient, the clinician or other qualified observer. Regression of a tumor in a patient is typically measured with reference to the diameter of a tumor. Decrease in the diameter of a tumor indicates regression. Regression is also indicated by failure of tumors to reoccur after treatment has stopped. In preferred embodiments, a decrease in tumor size or burden of at least 20%, more preferably 50%, 80%, 90%, 95% or 99% is preferred.

This invention further includes pharmaceutical combinations comprising a cell cycle checkpoint activator and an oncogenic kinase modulator as provided above and kits for the treatment of cancer patients comprising a vial of the anti-metabolite derivative and a vial of β-lapachone or a derivative or analog thereof at the doses provided above. Preferably, the kit contains instructions describing their use in combination.

The invention is further defined by reference to the following examples. It is understood that the foregoing detailed description and the following examples are illustrative only and are not to be taken as limitations upon the scope of the invention. It will be apparent to those skilled in the art that many modifications, both to the materials and methods, may be practiced without departing from the purpose and interest of the invention. Further, all patents, patent applications and publications cited herein are incorporated herein by reference.

EXAMPLES

Example 1

Method

β-lapachone was dissolved at 20 mM concentration in dimethyl sulfoxide (DMSO), aliquoted, and stored at −20° C. for cell culture use. Imatinib was dissolved at 100 mM concentration in dimethyl sulfoxide (DMSO).

ARH-77 cells, a human multiple myeloma cell line, were suspended in RPMI 1640 medium (Life Technologies Inc.), supplemented with 10% FCS, 2 mM L-glutamine, in 96-well plates (2×10$^4$ cells per well). Each well was treated with β-lapachone and/or imatinib. Each condition was run in triplicate. After incubation for 24 hours, cell survival was assayed using MTT to determine cell survival (see, e.g., Li Y. (2000) *Molecular Medicine.* 6(12):1008-1015). The plates were read using a plate reader at 570 nm.

Results

Figure 1A:
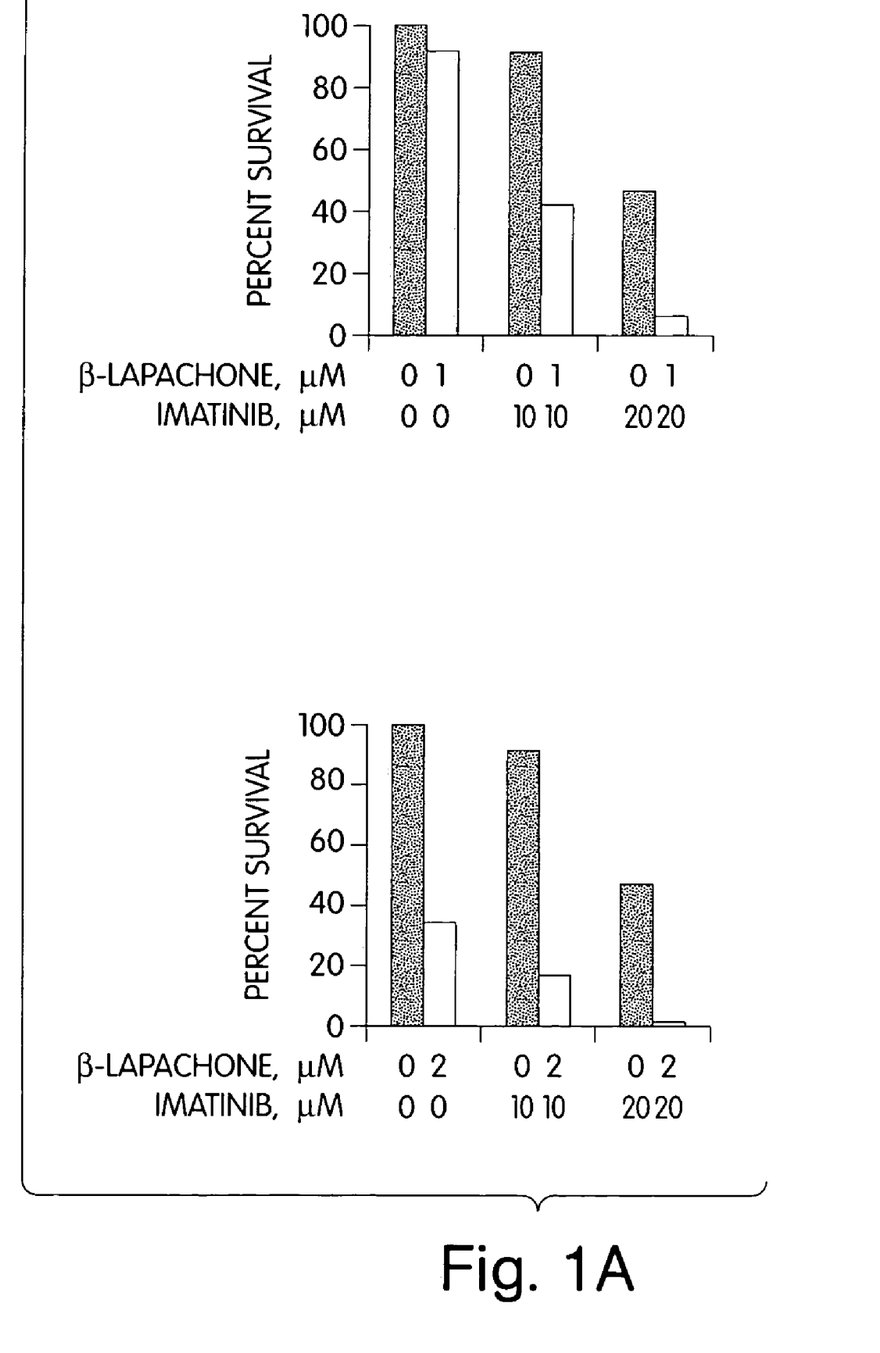
FIG. 1A shows the effect of combined treatment with β-lapachone and imatinib on human multiple myeloma cells.
Figure 1B:
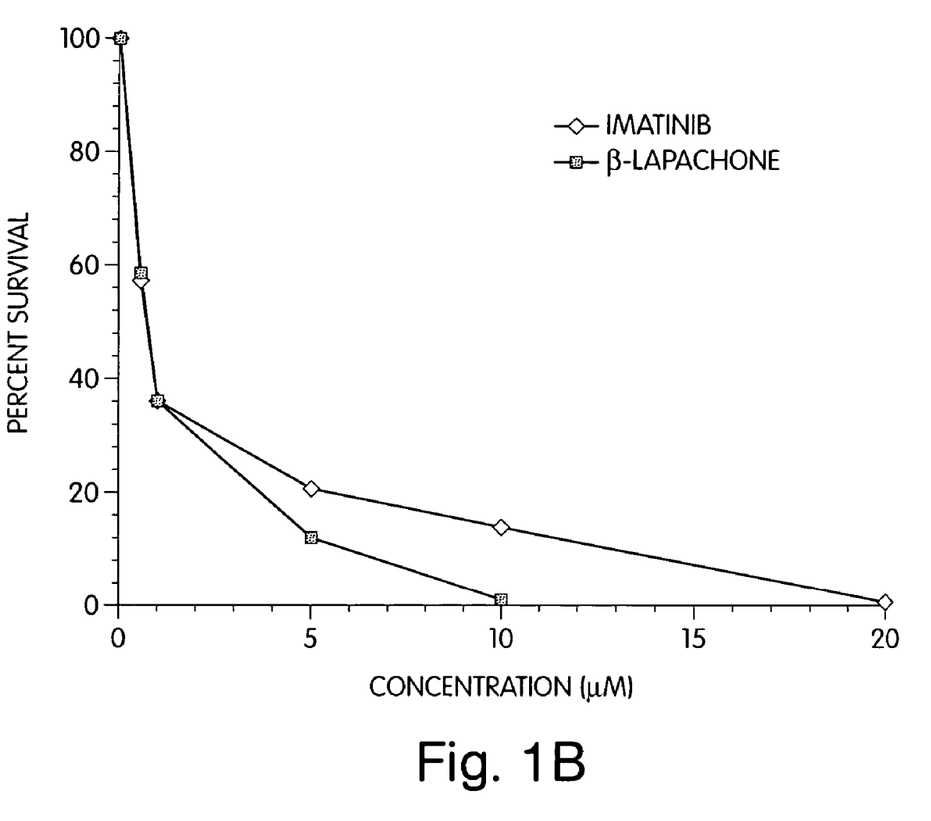
FIG. 1B shows the effect of treatment with β-lapachone or imatinib on human multiple myeloma cells.

The results are shown in FIGS. 1A and 1B and summarized in Table 3.

TABLE 3

| STI571(µM) | Co-501(µM) | % Viability |
|---|---|---|
| 0 | 0 | 100 |
| 1 | 0 | 66.3 |
| 2 | 0 | 80.0 |
| 5 | 0 | 85.7 |
| 10 | 0 | 91.0 |
| 20 | 0 | 46.7 |
| 50 | 0 | 10.0 |
| 100 | 0 | 1.3 |
| 0 | 1 | 91.4 |
| 0 | 2 | 34.3 |
| 0 | 4 | 40.0 |
| 10 | 1 | 42.2 |
| 20 | 1 | 17.7 |
| 10 | 2 | 6.7 |
| 20 | 2 | 2.0 |

Treatment of the myeloma cells with β-lapachone alone induced reduced cell survival from 100% (no β-lapachone) to 91% (1 uM β-lapachone) to 34% (2 uM β-lapachone). Treatment with imatinib alone also reduced cell survival, to 91% (10 uM imatinib) or 47% (20 uM imatinib). These myeloma cells were highly sensitive to the combination of β-lapachone and imatinib; the combination of 2 uM β-lapachone with 20 uM imatinib killed all but 2% of the cells. These results show that the combination of β-lapachone and imatinib has a synergistic effect in increasing ARH-77 cell death. The predicted percent viability for 1 µM β-lapachone and 10 µM imatinib if their effect was additive is 83%, but the actual percent viability is 42%. Likewise for predicted percent viability for 1 µM β-lapachone and 20 µM imatinib. If their effect was additive the percent viabiltiy would be 43%, but the actual percent viability is 7%. For 2 µM β-lapachone and 10 µM imatinib if their effect was additive the percent viability would be 31%, but the actual percent viability is 18%. For 2 µM β-lapachone and 20 µM imatinib if their effect was additive is the percent viability would be 16%, but the actual percent viability is 2%.

Example 2

Method

β-lapachone and imatinib were formulated as described in Example 1.

K562 cells (a human chronic myelogenous leukemia (CML) cell line), were suspended in RPMI 1640 Medium (Life Technologies Inc.), supplemented with 10% FCS, 2 mM L-glutamine in 96-well plates (2×10⁴ cells per well). Both an imatinib-sensitive and an imatinib-resistant cell line were used. Each well was treated with β-lapachone and/or imatinib. Each condition was run in triplicate. After incubation for 48 hours, cell survival was assayed using MTT to determine cell survival. The plates were read using a plate reader at 570 nm.

Results

Figure 2A:
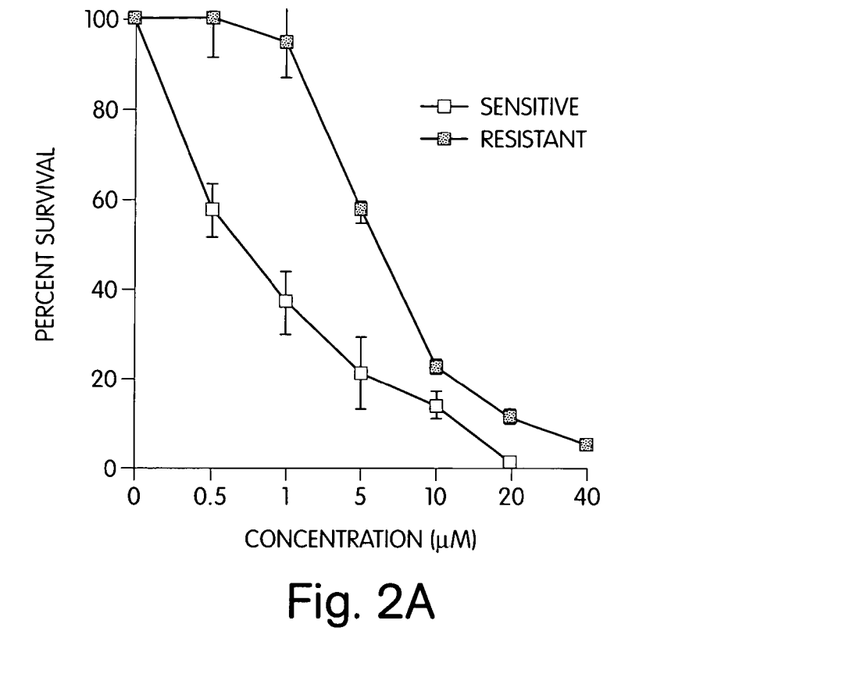
FIG. 2A shows the effect of treatment with β-lapachone or imatinib on human chronic myelogenous leukemia cell lines.
Figure 2B:
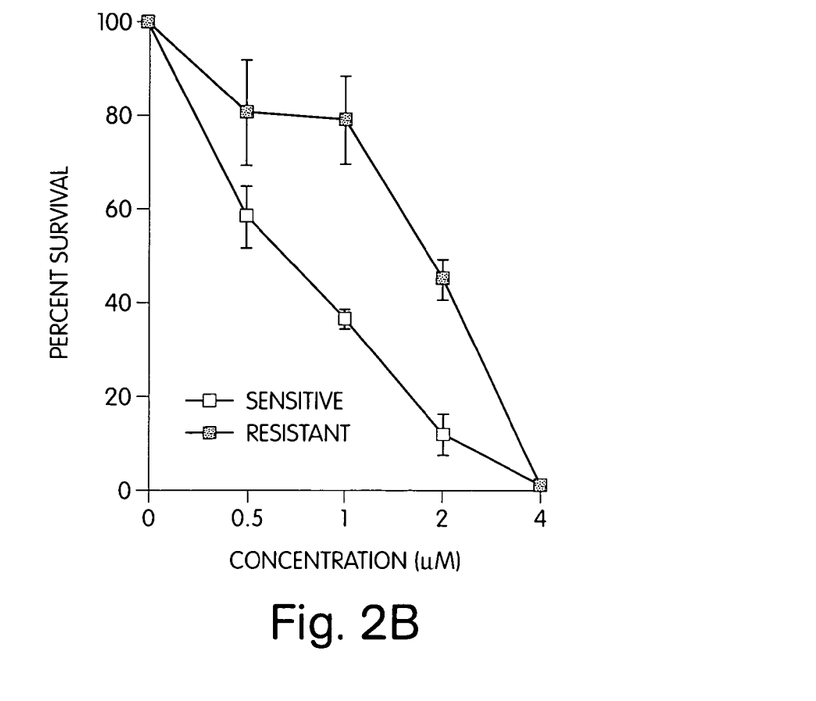
FIG. 2B shows the effect of treatment with β-lapachone or imatinib on human chronic myelogenous leukemia cell lines.
Figure 2C:
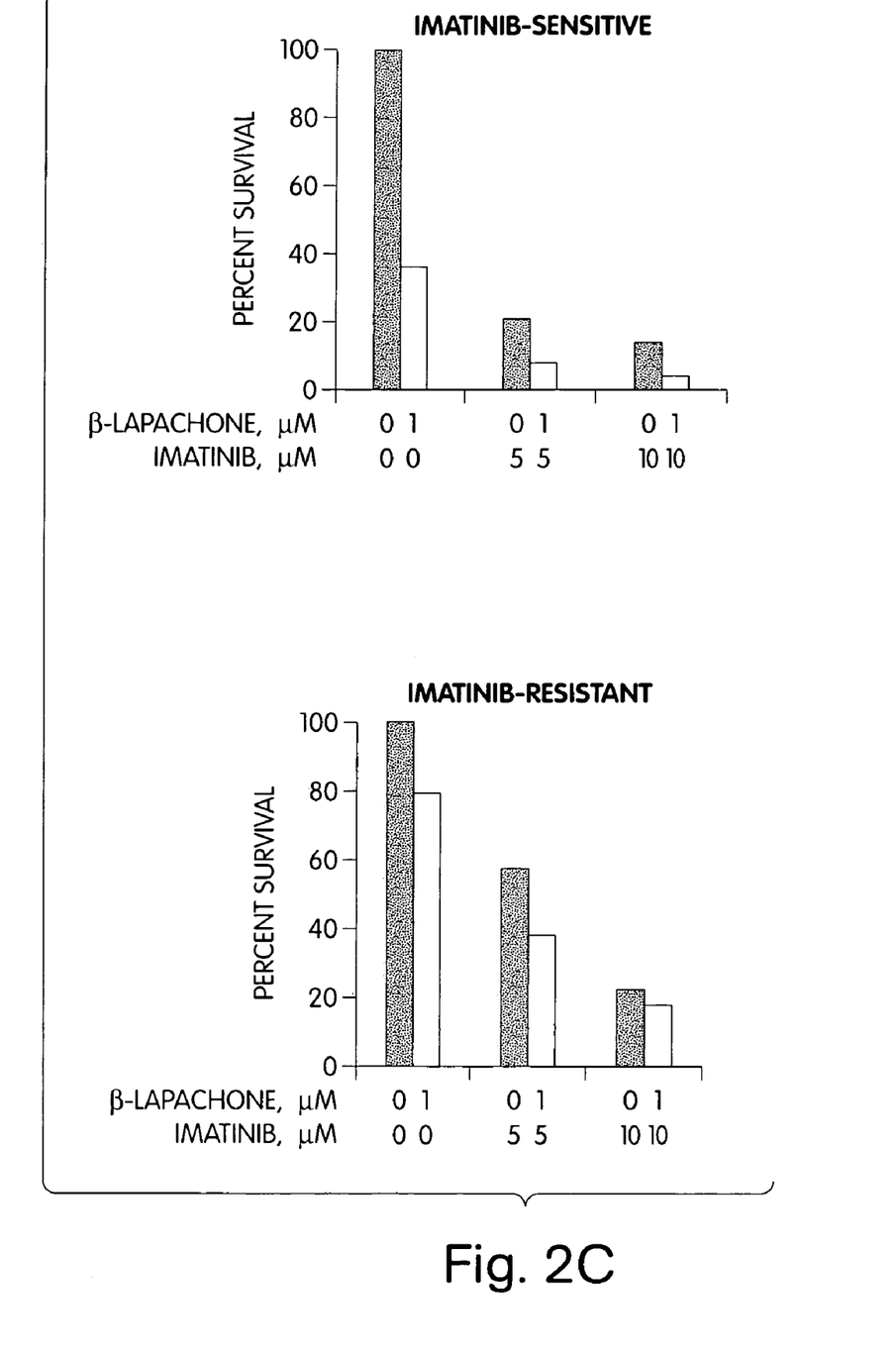
FIG. 2C shows the effect of combined treatment with β-lapachone and imatinib on human chronic myelogenous leukemia cell lines.

The results are shown in FIGS. 2A, 2B, and 2C and summarized in Tables 4 and 5.

TABLE 4

Imatinib senstitive cells.

| Imatinib (µM) | B-lapachone (µM) | % Viability |
|---|---|---|
| 0 | 0 | 100 |
| 0.5 | 0 | 57.2 |
| 1 | 0 | 36.6 |
| 5 | 0 | 20.9 |
| 10 | 0 | 13.9 |
| 20 | 0 | 0.9 |
| 0 | 0.5 | 58.3 |
| 0 | 1 | 36.2 |
| 0 | 2 | 11.9 |
| 0 | 4 | 1.0 |
| 1 | 5 | 8.4 |
| 1 | 10 | 4.6 |
| 1 | 20 | 4.0 |
| 2 | 5 | 3.96 |
| 2 | 10 | 2.9 |
| 2 | 20 | 3.8 |

TABLE 5

Imatinib resistant cells.

| Imatinib (µM) | B-lapachon (µM) | % Viability |
|---|---|---|
| 0 | 0 | 100 |
| 1 | 0 | 94.7 |
| 5 | 0 | 57.3 |
| 10 | 0 | 22.5 |
| 20 | 0 | 11.5 |
| 40 | 0 | 4.9 |
| 0 | 0.5 | 80.5 |
| 0 | 1 | 79 |
| 0 | 2 | 45 |
| 0 | 4 | 0.56 |
| 1 | 10 | 38 |
| 1 | 20 | 17.6 |
| 1 | 40 | 8.8 |
| 2 | 10 | 19.5 |
| 2 | 20 | 16.2 |
| 2 | 40 | 9.0 |

Treatment of the CML cells with β-lapachone alone induced reduced cell survival from 100% (no β-lapachone) to 58.3% (0.5 µM β-lapachone) to 11.9% (2 µM β-lapachone). Treatment with imatinib alone also reduced cell survival, with the imatinib-resistant lines showing less sensitivity, as expected. These CML cells were highly sensitive to the combination of β-lapachone and imatinib. The combination of 1 µM β-lapachone with 5 µM imatinib killed all but 8.4% of the imatinib sensitive cells.

Although the foregoing invention has been described in some detail by way of illustration and example for the purposes of clarity of understanding, one skilled in the art will easily ascertain changes and modifications may be practiced without departing from the spirit and scope of the appended claims.

All references described herein are incorporated by reference.

What is claimed is:

1. A method of treating multiple myeloma in a human, the method comprising administering to the subject a therapeutically effective amount of β-lapachone and imatinib, such that the multiple myeloma is treated.

2. The method of claim 1, wherein β-lapachone and imatinib are administered intravenously, orally or intraperitoneally.

3. The method of claim 1, wherein β-lapachone and imatinib are administered orally.

4. The method of claim 1, wherein imatinib is administered orally.

5. The method of claim 1, wherein β-lapachone is administered intravenously.

6. The method of claim 1, wherein imatinib is administered simultaneously with, preceding administration of, or following administration of β-lapachone.

7. The method of claim 6, wherein imatinib is administered following administration of β-lapachone.

8. The method of claim 7, wherein imatinib is administered within 24 hours after β-lapachone is administered.

9. The method of claim 1, wherein the therapeutically effective amount of β-lapachone is contained in a first vial, and imatinib is contained in a second vial, the contents of the first and second vials being administered to the patient simultaneously or sequentially.

10. The method of claim 1, wherein imatinib is administered at a dosage of approximately 400, 600 or 800 mg/day.

11. The method of claim 1, wherein β-lapachone is administered at a dosage from about 100 to 500,000 µg per kilogram body weight of recipient per day.

12. The method of claim 1, wherein β-lapachone is administered at a dosage from about 1000 to 250,000 µg per kilogram body weight of recipient per day.

13. The method of claim 1, wherein β-lapachone is administered at a dosage from about 10,000 to 150,000 µg per kilogram body weight of recipient per day.

14. The method of claim 1, wherein β-lapachone is administered at a dosage from about 2 mg/m² to 5000 mg/m² per day.

15. The method of claim 1, wherein β-lapachone at a dosage from about 20 mg/m² to 500 mg/m² per day.

16. The method of claim 1, wherein β-lapachone is administered at a dosage from about 30 to 300 mg/m² per day.

17. The method of claim 1, wherein β-lapachone further comprises a pharmaceutically acceptable carrier.

18. The method of claim 17, wherein the pharmaceutically acceptable carrier is a water solubilizing carrier molecule selected from the group consisting of Poloxamer, Povidone K17, Povidone K12, Tween 80, ethanol, Cremophor/ethanol, polyethylene glycol (PEG) 400, propylene glycol, Trappsol, alpha-cyclodextrin, beta-cyclodextrin, and gamma-cyclodextrin.

19. The method of claim 1, wherein the subject is human.

* * * * *

UNITED STATES PATENT AND TRADEMARK OFFICE
CERTIFICATE OF CORRECTION

PATENT NO.       : 7,361,691 B2  
APPLICATION NO.  : 10/726467  
DATED            : April 22, 2008  
INVENTOR(S)      : Chiang Li and Youzhi Li Page 1 of 1

It is certified that error appears in the above-identified patent and that said Letters Patent is hereby corrected as shown below:

In claim 15, column 26, line 47, "wherein β-lapachone at a" should read

-- wherein β-lapachone is administered at a --.

Signed and Sealed this

Eighth Day of July, 2008

JON W. DUDAS  
*Director of the United States Patent and Trademark Office*